United States Patent [19]
King et al.

[11] Patent Number: 5,514,596
[45] Date of Patent: May 7, 1996

[54] METHOD FOR INTRACAVITY SENSING OF MACROSCOPIC PROPERTIES OF CHEMICALS

[76] Inventors: David A. King, 1300 Waverly St., Palo Alto, Calif. 94301; Jens-Peter Seher, Remppesstr. 9, D-7000 Stuttgart 70, Germany

[21] Appl. No.: 419,653

[22] Filed: Apr. 10, 1995

Related U.S. Application Data

[62] Division of Ser. No. 227,932, Apr. 15, 1994.

[51] Int. Cl.$^6$ .................................................. G01N 21/41
[52] U.S. Cl. ........................... 436/164; 436/171; 436/172; 436/805; 356/352; 385/36
[58] Field of Search ..................................... 436/164, 171, 436/172, 805; 356/352; 385/36

[56] References Cited

U.S. PATENT DOCUMENTS

| | | | |
|---|---|---|---|
| 4,857,273 | 8/1989 | Stewart | 422/68 |
| 5,229,833 | 7/1993 | Stewart | 356/364 |

OTHER PUBLICATIONS

Steven J. Choquette et al. "Planar Waveguide Immunosensor With Fluorescent Liposome Amplification", 1992, vol. 64(1), pp. 55–60, *Analytical Chemistry*.
Wolfgang Demtröder, *Laser Spectroscopy*, Springer–Verlag, Berlin, 1982, pp. 390–395.
A. P. Godlevskii et al. "Intracavity Adsorption Spectroscopy of Surface-Active Substances, Adsorbed Gases, and Aerosols", 1979, vol. 29, pp. 1301–1304, *J. Appl. Spect.*
N. J. Harrick, *Internal Reflection Spectroscopy*, Interscience Publishers, New York, 1967, pp. 147–177.
J. H. Jerman et al. "A miniature Fabry–Perot interferometer with a corrugated silicon diaphragm support", 1991, vol. 29, pp. 151–158, *Sensors and Acutators*.
Thomas J. Kane et al. "Monolithic, unidirectional single–mode Nd:YAG ring laser", 1985, vol. 10, (2), pp. 65–67, *Optics Letters*.
R. P. H. Kooyman et al. "A fiber–optic fluorescence immunosensor", vol. 798, 1987, pp. 290–293, *Proc. Soc. Photo-opt. Instrum. Eng.*
William J. Kozlovsky et al. "Efficient Second Harmonic Generation of a Diode–Laser–Pumped CW Nd: YAG Laser Using Monolithic MgO: LiNbO$_3$ External Resonant Cavities", 1988, vol. 24 (6), pp. 913–919, *IEEE Journal of Quantum Electronics*.
Mel N. Kronick et al., "A New Immunoassay Based on Fluorescence Excitation by Internal Reflection Spectroscopy", 1975, vol. 8, pp. 235–240, *Journal of Immunological Methods*.
Y. Liu et al. "An Integrated Optical Sensor for Measuring Glucose Concentration", 1992, vol. B 54, pp. 18–23, *Applied Physics B*.
Paul Lorrain et al. *Electromagnetic Fields and Waves*, W. H. Freeman and Company, San Francisco, 1962, pp. 504–515.
W. Lukosz, "Principles and sensitivities of integrated optical and surface plasmon sensors for direct affinity sensing and immunosensing", 1991, vol. 6, pp. 215–225, *Biosensors and Bioelectronics*.
Konan Peck et al. "Single–molecule fluorescence detection: Autocorrelation criterion and experimental realization with phycoerythrin", 1989, vol. 86, pp. 4087–4091, *Proc. Natl. Acad. Sci. USA*.
Dror Sarid et al. "Optical field enhancement by long–range surface–plasma waves", 1982, vol. 21 (22), pp. 3993–3995, *Applied Optics*.
Anthony E. Siegman, *Lasers*, University Science Books, Mill Valley, California, 1986, pp. 524–527.
S. Schiller et al. "Fused–silica monolithic total–internal–reflection resonator", 1992, vol. 17 (5), pp. 378–380, *Optics Letters*.
A. N. Sloper et al. "A Planar Indium Phosphate Monomode Waveguide Evanescent Field Immunosensor", 1990, vol. B1, pp. 589–591, *Sensors and Acutators*.
Steven A. Soper et al. "Single–Molecule Detection of Rhodamine 6G in Ethanolic Solutions Using Continuous Wave Laser Excitation", 1991, vol. 63 (5), pp. 432–437, *Analytical Chemistry*.

*Primary Examiner*—Jeffrey R. Snay

[57] ABSTRACT

The presence of trace materials in a sample is detected using both macroscopic and microscopic properties. A detector includes a light source and an optical resonator. The light source may be located either inside the resonance cavity of the resonator or outside the cavity, in which case it may be a semi-conductor such as a semi-conductor laser or a superluminescent diode. The detector also includes at least one reflective member that has a total internal reflection (TIR) surface and may be a passive device or an active gain element. Light from the light source is preferably focussed onto a single point of reflection on the TIR surface. The test sample is positioned within the evanescent field region of the TIR surface. Optical changes arising within the evanescent field region, such as excitation of fluorescence in the sample, changes in its refractive index, and changes in the resonant frequency of the optical resonator, are then detected. These changes are then sensed to determine the amount or at least presence of analyte located at the TIR surface.

5 Claims, 9 Drawing Sheets

METHOD FOR INTRACAVITY SENSING OF MACROSCOPIC PROPERTIES OF CHEMICALS

This is a divisional of copending application Ser. No. 08/227,932 filed on Apr. 15, 1994.

BACKGROUND OF THE INVENTION

1. Field of the Invention

This invention involves a method and an apparatus for optically detecting trace chemicals near a sensor surface.

2. Description of the Related Art

Many branches of medicine, chemistry, and biology depend on an ability to assay chemical, biochemical, or biological samples, or to determine changes in the chemical composition of such samples. The diagnosis of many diseases, for example, often relies on the ability to detect the presence of antibodies in the blood.

As another example, using fluorometric analysis, one determines the amount of a fluorescing material present in a sample by measuring the intensity of the fluorescence emitted from the material. Such fluorometric techniques are particularly useful in biochemical assays that test for the presence of fluorophores.

There are accordingly many different methods and devices for detecting the presence or measuring the amount of chemicals in a bulk sample. These devices are well understood and have been widely used. Examples of these devices are described in the books *Laser Spectroscopy*, Demtroder, W., Springer-Verlag, Berlin, 1982, and *Fluorescence and Phosphorescence*, Rendell, D., John Wiley, Chichester, 1987.

Other known chemical sensors involve optical absorption spectroscopy. These spectroscopic analyzers typically use one of two techniques: 1) sensing of interferences between multiple reflections in thin films, as is described in *Internal Reflection Spectroscopy*, Harrick, N.J., Wiley, New York, 1967; and 2) total internal reflection (TIR) absorption spectroscopy inside a laser cavity, as is described in "Intracavity adsorption spectroscopy of surface-active substances, adsorbed gases, and aerosols," Godlevskii, A.P., and Kopytin, Yu. D., J. Appl. Spect., 29, 1301 (1978).

Harrick describes the use of constructive interferences in thin film "cavities" to increase the sensitivity of optical absorption spectroscopy. Light is coupled into a thin film where it undergoes multiple (total internal) reflections. If a wide light beam is used, then multiply reflected beams may constructively interfere with the directly reflected beam. Harrick points out, however, that many problems exist for this structure: precise angles of incidence need to be maintained, effective improvement is limited by the actual size of the beam, and critical matching of surface reflectivities is essential for optimum enhancement.

Recent work has shown that the latter limitation can be relieved. U.S. Pat. No. 4,857,273 (Stewart, 15 Aug. 1989, "Biosensors"), for example, illustrates improvements over the Harrick system. Other problems, however, so limit the sensitivity of this structure that they render it practically useless as a highly sensitive transducer for small sensing areas. Many of these problems stem from the fact that the Stewart sensor employs a form of resonant waveguide and thus requires a long interaction length so that light will "bounce" enough times within the waveguide. To make the device smaller, one would have to shorten the interaction length. This would, though, also reduce the length over which light could bounce and would cause the sensor to lose much of its sensitivity.

Godlevskii and Kopytin describe a system in which a total reflecting cell is placed inside a laser resonator. The output laser power is then measured as molecules are adsorbed to the TIR surface. The molecules are assumed to have an optical absorption at or near the laser frequency, which means that they will act as an additional intracavity loss mechanism. While both the Harrick and Godlevskii systems use "optical cavities," only the latter offers an optical resonator that is stable enough to solve many of Harrick's problems.

On the other hand, the Godlevskii/Kopytin system confines itself to absorption spectroscopy of simple molecules. In order for the Godlevskii/Kopytin system to work properly, it must therefore have enough molecules of the analyte to provide detectable absorption. Because of this, the sensitivity of the Godlevskii/Kopytin system is limited to detection of surface concentrations greater than those at which the intracavity field is significantly perturbed. Since this system relies on having enough absorbing molecules of the analyte to perturb the electric field at the TIR boundary, the system is not able to detect concentrations or molecules much below this limit.

According to another known technique, trace chemicals are detected using fluorescence. A method for detecting biomolecules using fluorescence at a TIR surface is, for example, described in the article "A new immunoassay based on fluorescence excitation by internal reflection spectro-scopy," by Kronick, M. L., and Little, W. A., J. Immunological. Meth., 8, 235 (1975). According to this technique, a prism is mounted in free space, not within a resonant cavity. Because of this structure, light is deliberately "discarded," that is, its energy is not used to contribute further to fluorescence, after it is reflected off of the TIR surface. This in turn means that the Kronick system requires large and powerful light sources in order to achieve sufficient fluorescent excitation for high sensitivity.

Other detection systems and techniques that use fluorescent excitation are described in the following references:

1) Sloper, A. N., Deacon, J. K., and Flanagan, M. T., "A planar indium phosphate monomode waveguide evanescent field immunosensor," Sensors and Actuators, B1, 589 (1990), (describing the use of waveguides);

2) Choquette, S. J., Locascio-Brown, L., and Durst, R. A., "Planar waveguide immunosensor with fluorescent liposome amplification," Anal. Chem., 64, 55 (1992), (also using waveguides); and 3) Kooyman, R. P. H., de Bruijn, H. E., and Greve, J., "A fiber-optic fluorescence immunosensor," Proc. Soc. Photo-Opt. Instrum. Eng., 798, 290 (1987), (describing the use of optic fibers).

As in the Kronick method, these three techniques do not "recycle" light within a cavity, and are thus similarly limited either to needlessly large light sources or to reduced sensitivity.

By definition, the less of a material a detector needs in order to detect it, the more sensitive the detector will be. Consequently, it is a standing goal to increase the sensitivity of detectors.

There is a well-recognized need for techniques that an rapidly detect minute amounts (for example, fewer than $10^5$ molecules), of biomolecules without either radioactive labeling or chemical amplification (such as polymerase chain reaction). Single molecules have been detected optically using methods described in Peck, K., Stryer, L., Glazer, A. N., and Mathies, R. A., "Single molecule fluorescence detection: Autocorrelation criterion and experimental realization with phycoerythrin," Proc. Natl. Acad. Sci. USA, 86, 4087 (1989), and Soper, S. A., Brooks Shera, E., Martin, J. C., Jett, J. H., Hahn, J. H., Nutter, H. L., and Keller, R. A., "Single-molecule detection of rhodamine 6G in ethanolic solutions using continuous wave laser excitation," Anal. Chem., 63, 432 (1991). The problem with these methods, however, is that they are very difficult to produce commercially, since they, too, require large lasers (with accompanying large power supplies and in some cases cooling systems), to generate a sufficiently strong electric field.

Apart from the question of sensitivity, many existing detection systems also suffer from the problem that they are bulky or are difficult to control electronically. This means not only that they are less accessible to small laboratories, which may have neither the space nor the money to buy and install one, but also that they will be harder to use and control properly if they are installed.

What is needed is a method for surface (rather than only bulk), detection that makes it possible to detect sample concentrations of molecules even less that those for which the intracavity field is perturbed. The detection system itself should be stable, compact, easily calibrated, and easily controlled.

SUMMARY OF THE INVENTION

The invention provides methods and a corresponding detection apparatus for detecting the presence of a target substance in a sample using both macroscopic properties (such as changes in the refractive index of the analyte), and microscopic properties (such as the presence of a fluorescing indicator), with a sensitivity that is at least an order of magnitude greater than the sensitivity of systems such as those described above.

According to the invention, the detection system includes a light source, such as a laser, and an optical resonator that has a resonant cavity for light generated by the light source. The light source may be located either within the cavity, or outside of the cavity, in which case it may be a gain medium such as a semiconductor laser or a superluminescent diode. The detector according to the invention also includes at least one reflective element or member. The reflective element or member, which may be a passive device such as a prism, a waveguide, or a fiber, or an active gain element such as a doped optical fiber, has a total internal reflection (TIR) surface and is itself located within the cavity. The TIR surface may alternatively be formed by a separate element that is removable from and is optically coupled to the reflective element.

Light from the light source passes into the reflective element and is reflected by the TIR surface, preferably at a single point of reflection; an evanescent field region is thereby formed at the TIR surface. The sample to be tested is positioned so that it extends into the evanescent field region. Any conventional arrangement may be used to introduce, contain, and position the sample.

The invention further provides a detector for detecting predetermined optical changes arising within the evanescent field region, typically no more than about one optical wavelength of the light source away from the TIR surface. These changes include excitation of light frequency changes (such as fluorescence) within the sample, changes in its refractive index, and changes in the resonant frequency of the optical resonator. These changes are then sensed to determine the amount or at least presence of analyte located at the TIR surface.

BRIEF DESCRIPTION OF THE DRAWINGS

FIG. 6 is an example of a plot of the ratio of reflected light intensity to the incident intensity from a TIR surface in a detector according to the invention as a function of the increase in the refractive index due to the presence of an analyte;

DETAILED DESCRIPTION

Figure 1:
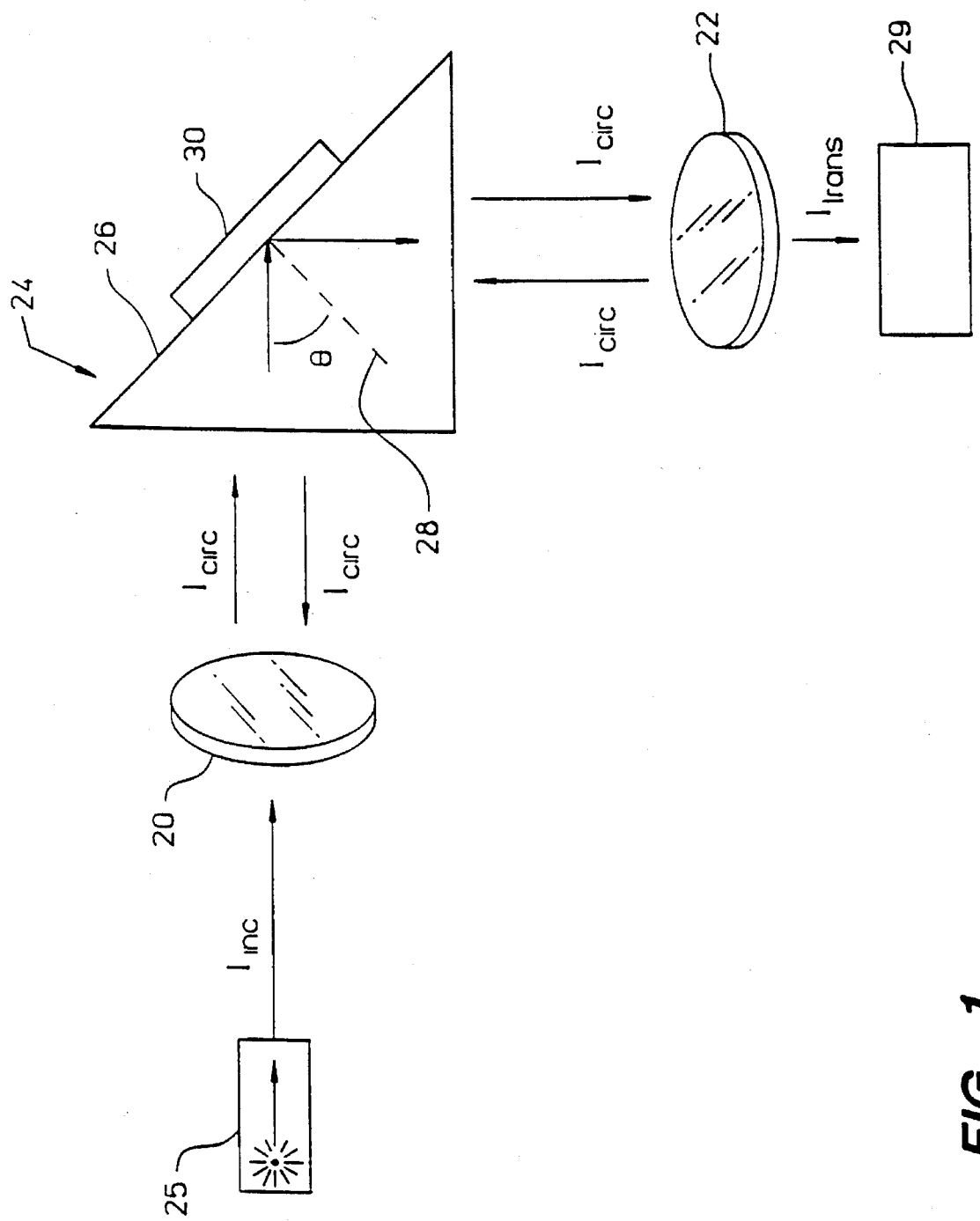
FIG. 1 illustrates schematically the main components of a detector according to the invention, with a standing-wave optical resonator and a single total internal reflection (TIR) surface.

First, some of the theory underlying the invention is explained. Then, various embodiments of the invention are described. These embodiments make use of the method of the invention for chemical detection of microscopic and macroscopic properties of a sample or, more specifically, of a target substance (chemical) contained within the sample. Examples of target substances that the invention is exceptionally well suited to detect include antibodies, drugs, polynucleotides, cell membrane receptors, sugars, nucleic acids, or even synthetic molecules; the target substance may also be a gas.

Theoretical Foundation of the Invention

In order to understand the advantages of the invention, it is helpful first to understand the structure and function of an optical resonator, as well as certain principles of optics. These concepts are therefore reviewed briefly.

As light travels through a medium it may be totally reflected when it strikes an interface with another medium of lower refractive index. This phenomenon is termed total internal reflection (TIR) and occurs for angles of incidence greater than a critical angle, $\theta_c$. The electromagnetic field then no longer propagates in the second medium but rather exponentially decays away from the interface.

In its simplest form, an optical resonator or cavity consists of several mirrored surfaces arranged so that incident light is trapped and bounces back and forth between the mirrors. As an example, consider the case where one of the mirrors is a prism with a face (a TIR surface) that totally reflects the light beam within the resonator cavity (the intracavity beam). At the point of reflection on the prism surface, an evanescent wave is generated with a characteristic decay depth typically of one optical wavelength. At the TIR surface, the light is confined to the surface and it interacts only with chemicals within the decay depth of the surface.

As is well known in the field of optics, an electromagnetic wave is evanescent in a particular direction when it maintains a constant phase in that direction but has exponentially decreasing amplitude. In the case of TIR, light in the form of an infinite plane wave establishes an exponentially decreasing, evanescent electromagnetic field beyond an infinite, planar TIR surface boundary. Although the electric field has velocity components in the plane of the TIR boundary, there is no velocity component perpendicular to and beyond this boundary. In other words, for the idealized case, only a potential gradient is established beyond a TIR boundary; no energy is actually transported beyond the boundary.

In practical applications, of course, neither the incident electromagnetic field nor the TIR surface is infinite. For such finite configurations, it is known that some light diffracts within the boundary, that is, some energy will flow to just beyond the boundary, but will "curve back" toward the boundary, reenter the initial medium, and then exit a small distance away from its entrance point; this is known as the Goos-Hänchen effect. In most devices that employ TIR surfaces, such as this invention, this shift is negligible. The large electromagnetic potential gradient beyond the boundary, however, remains.

FIG. 1 is a simplified schematic illustration of a standing-wave optical resonator used according to the invention. In the simplified embodiment of the invention shown in FIG. 1, it is assumed that a light source is located outside of the resonator cavity (examples of other systems are illustrated and discussed below). As FIG. 1 shows, the simple optical resonator includes an entrance mirror 20, an exit mirror 22, and a reflective element 24, which has a TIR surface 26. The mirrors 20, 22 may be either flat or curved and are chosen using conventional criteria to be suitable for generating a stable cavity field, which is well-known in the art. Suitable, stable cavity fields may also be generated using a configuration with more than two mirrors.

Light is generated by a conventional light source 25, which is preferably a coherent gain medium. The light source 25 may be either external to the resonator cavity, as is shown in FIG. 1, or may be incorporated within the cavity, as is described and shown below. For embodiments of the invention that use an external light source, the light that enters the cavity has an incident intensity $I_{inc}$. In this case, the light source may also include other known optical components that enable it to generate a stable cavity field. In all embodiments, the intensity of the circulating field just inside the entrance mirror 20 is $I_{circ}$.

An angle of incidence is defined as the angle $\theta$ between the path of light incident on the TIR surface and the normal (indicated by the dotted line 28 perpendicular to the surface 26), to the TIR surface at the point of incidence. For the sake of simplicity of explanation and analysis only, the TIR surface 26 is shown as being a plane. This is not necessary to the invention; the definition of angles of incidence for non-planar or piece-wise planar surfaces is well known in the field of optics. It is known that chemical changes at the TIR surface 26 influence optical properties of the resonator. These properties, which are explained below, underlie at least some of the embodiments of this invention and form the basis of the transducer that the invention provides.

In order to provide a foundation for determining the sensitivity of the various embodiments of the invention described below it is useful to determine the intensity of the electromagnetic fields both inside and transmitted by the resonator. Merely for the sake of simplicity, the following analysis considers only one TIR surface within the resonator cavity. Those skilled in the art could, however, readily extend the analysis using known mathematical techniques to include many TIR surfaces. In the structure shown in FIG. 1, for example, the reflective element 24 may be a waveguide or fiber, in which case there may be several TIR surfaces. This invention relates to detection systems with any number of intracavity TIR surfaces.

FIG. 1 is a schematic representation of an embodiment of the invention with a single TIR surface within the resonator cavity. In this embodiment, the reflective element or member 24 is shown as being a prism, so that the TIR surface 26 is one face of the prism. Note that if the reflective element is chosen to be a prism, it is not necessary for it to be a right prism. Moreover, it is not necessary to the invention that the TIR surface be planar; as is pointed out above, the TIR surface may be curved (for example, for certain optical fibers), or piecewise planar or both.

As is discussed in greater detail below, a prism is just one example of a suitable TIR element; other examples are waveguides and fibers. Additionally, the TIR surface 26 can be on an optically transparent substrate surface such as a glass slide, optical film, or waveguide, that is optically coupled with the TIR element in a conventional manner, for example, using a compressible optical polymer or index matching oil. The substrate surface may be removable from the TIR element, and may even be disposable. If the test sample is attached directly to the TIR element, such as the prism, it may be necessary to clean or replace the prism before testing for another substance, and the alignment of the prism will then have to be checked and possibly readjusted. Providing a removable substrate eliminates or at least greatly reduces the cost and effort involved in ensuring that the prism is clean and aligned.

To simplify the analysis further, assume that all electromagnetic fields within the resonator are plane waves. Again, those skilled in the art of optics will readily be able to extend the analysis to embodiments of the invention for which this assumption is not valid. The power reflection coefficient, $R_i$, of the $i^{th}$ mirror (in the general case with i mirrors), is given by $R_i = r_i^2$ (for the two-mirror embodiment shown in FIG. 1, i=1,2). Now assume that the reflective element 24 (in the illustrated embodiment, a prism), has low-loss entrance and exit faces. The reflection coefficient of the prism is therefore $R_p = |r_p|^2$, and is determined only by the TIR surface 26.

According to the invention, a sample 30 to be analyzed is located immediately adjacent to the TIR surface 26. As is explained below, the sample is preferably located within about one optical wavelength of the TIR surface.

Figure 2A:
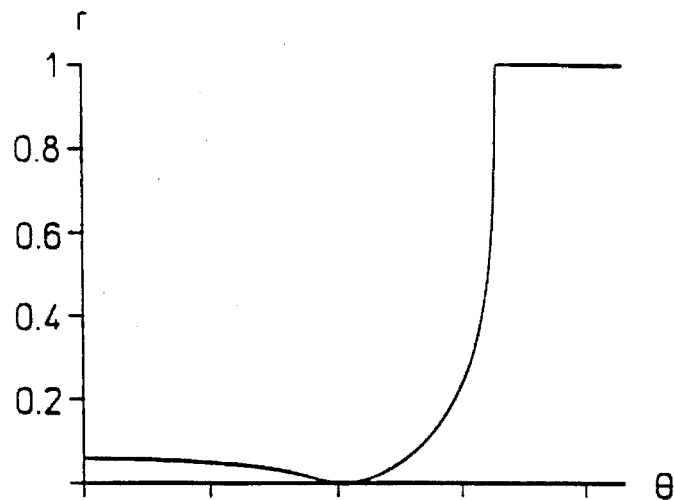
FIGS. 2a, 2b, and 2c illustrate graphically the relationship between the magnitude, phase, and penetration depth, respectively, for light incident on a TIR surface.
Figure 2B:
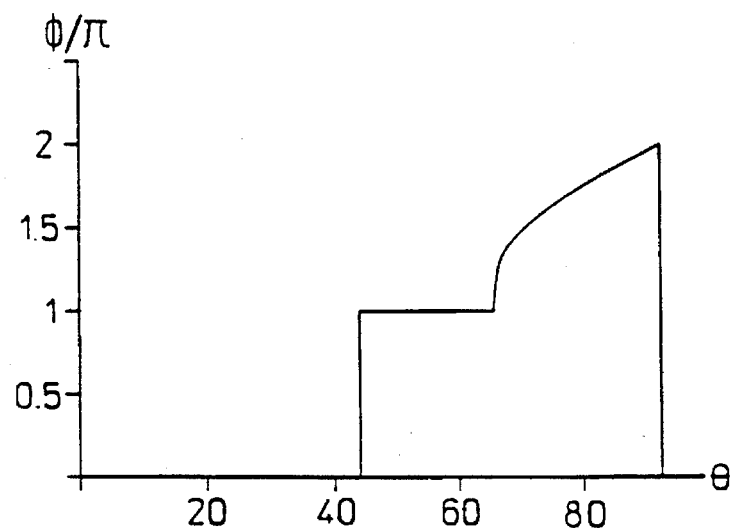
Figure 2C:
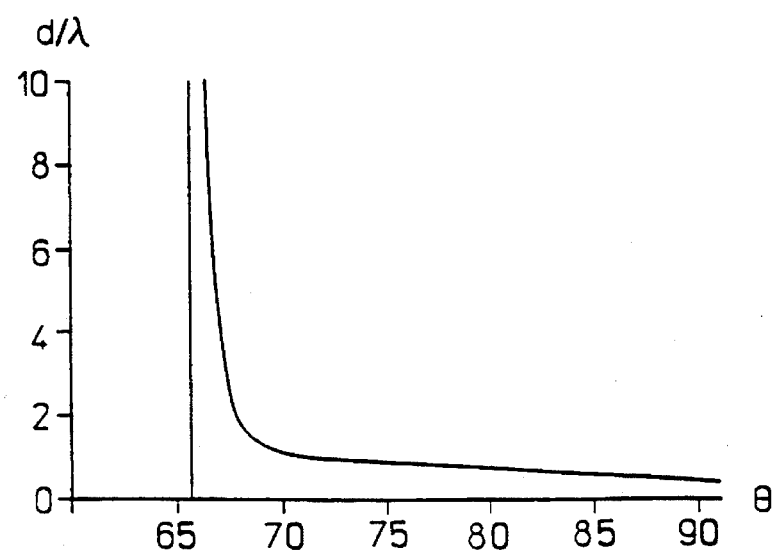

The optical properties of the sample 30 on the TIR surface 26 are described by the sample refractive index $n_s$. The value of $r_p$ depends on $n_s$, on the refractive index of the prism (or other reflective element), $n_p$, and finally on the angle of incidence, $\theta$. For TM or parallel polarized light, it can be shown (see, for example, Lorrain, P. and Corson, D., *Electromagnetic Fields and Waves*, W. H. Freeman, San Francisco, 1970), that:

$$r_p = \frac{\pm\sqrt{n^2 - \sin^2\theta} - n^2\cos\theta}{\pm\sqrt{n^2 - \sin^2\theta} + n^2\cos\theta} \qquad \text{Eqn. 1}$$

where $n = n_s/n_p$. For $\sin\theta > n$ (i.e. $\theta > \theta_c$, TIR), $r_p$ is complex, and the negative sign in front of the square root applies. The value of $r_p$ may be expressed more usefully in phasor notation: $r_p = re^{j\phi}$. When TIR occurs, $r=1$, the reflected light has a phase shift $\phi$, and $R_p = 1$. FIGS. 2a and 2b depict $r(\theta)$ and $\phi(\theta)$, respectively, for an interface between fused silica ($n_p = 1.457$) and water ($n_s = 1.33$). The penetration depth $d(\theta)$, expressed in units of wavelength, over which the intensity of the evanescent field drops to its 1/e point is given by the expression $d = \lambda/F(\theta)$, where $F(\theta) = 4\pi n_p(\sin^2\theta - n^2)^{1/2}$, and $\lambda$ is the wavelength of the incident light. FIG. 2c shows a plot of $1/F(\theta)$. The penetration depth is about one wavelength at large angles of incidence, while at the critical angle it is infinite (in this approximation).

The power transmission coefficient $T_i$ for the ith of a series of p reflective elements is given by $T_i = 1 - R_i$; $i = 1, 2, \ldots, p$ (in FIG. 1, only one is shown —the prism 24 —so that $p=1$). For a given light intensity, $I_{inc}$, incident on the resonator, the intensity, $I_{circ}$, of the circulating field just inside the entrance mirror 20 (FIG. 1) is determined by the ratio:

$$\frac{I_{circ}}{I_{inc}} = \frac{T_1}{\left|1 - r_1 r_2 r_p^2 \exp\left(-\alpha L - \frac{j\omega L}{c}\right)\right|^2} \qquad \text{Eqn. 2}$$

where $\alpha$ is the voltage absorption coefficient in the resonator, L is the round-trip path length, and $\omega$ is the angular frequency of the light. (See, for example, Siegman, A. E., *Lasers*, University Science Books, Mill Valley, Calif., 1986.) Eqn. 2 applies strictly only just inside the entrance mirror 20, but for a low-loss standing-wave resonator such as that depicted in FIG. 1, the average intensity is approximately $2 \cdot I_{circ}$ anywhere in the resonator.

Proceeding from equation Eqn. 2, it can easily be shown that if $r_p^2 = 1$ (that is, simple reflection from a mirror), then $I_{circ}$ will be at a maximum for frequencies $\omega = \omega_m$ that satisfy the equality:

$$\frac{\omega_m L}{c} = 2\pi \cdot m; \quad m = 1, 2, \ldots \qquad \text{Eqn. 3}$$

Equation Eqn. 3 defines the resonant mode frequencies, $\omega_m$, of the resonator. These frequencies are separated from one another by a value $2\pi c/L$, which is commonly termed the mode spacing.

Observing that $r_p^2 = r^2 e^{2j\phi}$ and substituting for $r_p$ in equation Eqn. 2 gives:

$$\frac{I_{circ}}{I_{inc}} = \frac{T_1}{\left|1 - r_1 r_2 r^2 \exp\left(-\alpha L - \frac{j\Omega L}{c}\right)\right|^2} \qquad \text{Eqn. 4}$$

where $\Omega = \omega - (2\phi c)/L$.

Similarly, the intensity, $I_{trans}$, of the light transmitted through the resonator is given by the ratio:

$$\frac{I_{circ}}{I_{inc}} = \frac{T_1 T_2 r^2 \exp(-\alpha L)}{\left|1 - r_1 r_2 r^2 \exp\left(-\alpha L - \frac{j\Omega L}{c}\right)\right|^2} \qquad \text{Eqn. 5}$$

As FIG. 1 illustrates, in those embodiments of the invention that detect the presence of chemicals based on $I_{trans}$ or some other property of the light that exits the cavity, a conventional detector 29, as well as accompanying conventional signal conversion and processing circuitry (not shown), is included adjacent to the exit mirror 22. For embodiments that measure the intensity $I_{trans}$ of the transmitted light, the detector 29 will be a suitable intensity-measuring device. As is discussed below, other types of detectors will be included when other properties are measured.

The effect of the phase shift $\phi$ due to TIR is to increase the resonant frequency $\omega_m$ of the resonator, which can be expressed as:

$$\omega_m = \frac{2c}{L}(\pi m + \phi); \quad m = 1, 2, \ldots \qquad \text{Eqn. 6}$$

As FIG. 2b shows, there is a phase shift of $\pi$ at the Brewster angle (42.4°). Furthermore, the phase begins to increase once TIR occurs. The maximum phase shift is $2\pi$, so that the resonant frequency changes by at most two mode spacings. Note that this analysis does not include the very slight phase shifts that can occur on reflections from real mirrors. The phase shifts caused by the mirrors are much less than $\pi$, are generally constant, and can therefore be ignored in all practical cases.

As the discussion above explains, and as is borne out by experiment, the evanescent field generated at the point of TIR is extremely sensitive to the optical properties of the surrounding chemical environment. This invention applies this theory to provide a detector that is at least an order of magnitude more sensitive than conventional systems, and which can do so using only surface (as opposed to bulk) samples.

Throughout the literature many different structures (such as Harrick's) have been termed resonant optical cavities based solely on the fact that they make some use of constructive interference of light waves. A constructive interference alone, however, is not sufficient to create a practical optical transducer with a high sensitivity.

The figures show linear resonators solely for the purpose of illustration; however, even for non-linear resonators (such as a ring resonator), the method of the invention will be the same: an analyte or sample to be analyzed is placed within the region of the evanescent field of a TIR surface, which is a surface of a reflective element located within the cavity of an optical resonator.

The choice of optical resonator used in a particular application of the invention will be a design option and will depend on the needs and characteristics of that application. In many applications, more complex resonators, such as those described by Siegman, may be more suitable than the simple resonator shown schematically in the figures here.

Examples of suitable resonators include Fabry-Perot, "V"-shaped, Michaelson-mirror, Fox-Smith, and Sagnac. The great advantage of these structures is that they generate stable and low-loss optical modes. This means that more of the available light can be utilized for sensing applications. Furthermore, while most useful resonators have Gaussian beam profiles, the analysis used above assumes plane waves. As is mentioned above, however, this assumption is made merely for the sake of clarity and simplicity and can be extended to non-planar embodiments. In other words, the results one obtains using the assumption of plane waves are essentially the same as for more complicated configurations, but the analysis is greatly simplified.

Using a diode laser as a light source, one could also construct an entirely integrated solid-state transducer suitable for use in the invention. The invention may also incorporate a resonator that is pumped at one wavelength and that generates another wavelength inside the cavity (see, for example, Kozlovsky, W. J., Nabors, C. D. and Byer, R. L., "Efficient second harmonic generation of diode-laser-pumped cw Nd:YAG laser using monolithic MgO:LiNbO3 external resonant cavities," IEEE J. Quant. Elec., 24, 913 (1988)); this would make possible the use of a high power source at different wavelengths.

There are many reflective elements with suitable TIR surfaces that could be incorporated within an optical resonator according to the invention. Examples include: 1) prisms (for example, a Dove prism); 2) fibers, either with optical gain (such as a fiber laser), or without; and 3) waveguides. Monolithic resonators could also be fabricated from a single piece of an appropriate material or by coating appropriate mirror surfaces on the end faces of a fiber or waveguide. For example, in fields unrelated to chemical sensing, Kane, T. J. and Byer, R. L., in "Monolithic, unidirectional single-mode Nd:YAG ring laser," Opt. Lett., 10, 65 (1985), describe a monolithic nonplanar ring resonator. Similarly, a miniature monolithic ring resonator with a finesse of 5100 is described in the article "Fused-silica monolithic total-internal-reflection resonator", Schiller, S., Yu, I. I., Fejer, M. M., and Byer, R. L. ., Opt. Lett., 17, 378 (1992), and in U.S. Pat. No. 5,038,352 (Lenth and Risk, 6 Aug. 1991).

Embodiments of the Invention for Detection of Microscopic and Macroscopic Sample Chemical Properties Different configurations of the invention can be used for different types of surface chemical sensing, depending in part on the properties of the optical resonator used in the system. In particular, the method according to the invention can be used in detector embodiments that sense the interaction of light in the resonator with microscopic and macroscopic properties of the analyte. Microscopic properties of the sample to be analyzed include interactions of light with single atoms or molecules, such as fluorescence. Macroscopic properties involve interactions of light with an ensemble of atoms or molecules, such as the refractive index of the analyte.

The sensitivity of a transduction technique based on microscopic properties is far greater than that based on macroscopic properties, simply because one requires a large number of particles to generate a macroscopic phenomenon. In other words, a detection method will not be able to detect only a few molecules if it requires many molecules just to produce a result. In both cases, however, the sensitivity of the invention is improved if one attaches an appropriate tag molecule or complex, such as a fluorophore, to the analyte.

Intensity-Dependent Evanescent Sensing (Microscopic Sensing Properties)

For optical-based transduction methods of microscopic properties, the signal, for example fluorescence, depends on the intensity of the electromagnetic field. The sensitivity is very often limited by the noise equivalent power of the detector. An increase in intensity reduces the amount of analyte that is necessary to generate the noise equivalent signal, thereby increasing the sensitivity. In simpler terms, the more power the system has available, the less of the analyte it needs in order to detect it. This remains true as the power increases, until saturation or quenching effects begin to play a role.

One way to increase power is to use a more intense light source, but this increases electrical power consumption and the physical size of the detector. This invention, however, makes use of the property that the intensity of the electromagnetic field inside the cavity of an optical resonator is often many orders of magnitude larger than the incident intensity. This increase in intensity can be demonstrated by evaluating Eqn. 2, assuming no intracavity losses ($\alpha$=0), equal mirror reflectivities, $R=R_1=R_2$, $\theta>\theta_c$ (that is, TIR), and that the incident light frequency is tuned to a cavity resonance. For these conditions, Eqn. 2 reduces to $I_{circ}/I_{inc}=1/(1-R)$.

Mirrors are readily available that have losses as low as 20 ppm (R=0.99998), resulting in a theoretical intracavity amplification factor of $I_{circ}/I_{inc}=1/(1-R)= 50,000$. Although other intracavity losses decrease this number, one can easily achieve experimental amplification factors of greater than $10^3$ using the invention and commercially available mirrors.

Figure 3:
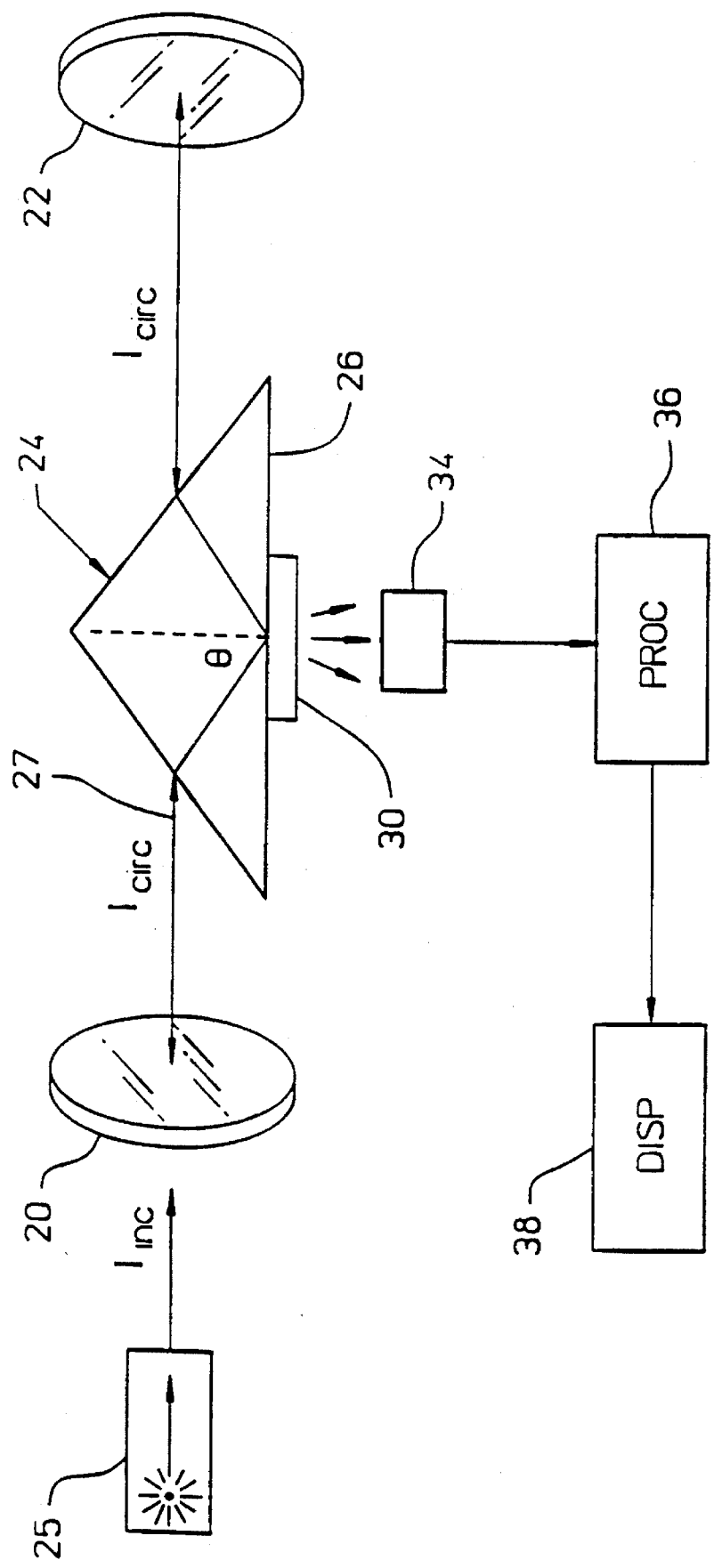
FIG. 3 shows schematically an embodiment of the invention that generates fluorescence from a fluorescent analyte located in an evanescent field, in which the evanescent field is created by TIR of an intracavity beam in a resonator pumped by a light source not within the resonator cavity itself.

FIG. 3 illustrates schematically an embodiment of the invention that uses an external light source. Features of this embodiment that are functionally the same as those described in FIG. 1 have the same reference numbers in FIG. 3 as they have in FIG. 1. The source 25 is frequency-locked to the resonant frequency of the cavity using techniques that are well known in the art.

Because the invention can, and preferably does, operate with a light source that is external but frequency-locked to the cavity, the light source may be a semiconductor such as a diode laser or a superluminescent diode. This gives the invention a great advantage over conventional systems such as that described by Godlevskii/Kopytin, in which the laser gain medium is inside the optical resonator. Diode lasers and other semiconductor light-generating devices are miniature devices that typically require ten to one hundred times less current than internal gain media and, when coupled to an external resonant optical cavity as in this invention, they can be operated with the same or even higher intracavity power. Systems with an internal gain medium, such as Godlevskii/Kopytin's, cannot use such compact semiconductor devices as their light source, since these devices typically cannot withstand the strong field that is generated within the cavity. Systems such as Godlevskii/Kopytin's are thus limited in that they provide no way to employ diode lasers and maintain high sensitivity through large intracavity power. Semiconductor light sources such as diode lasers also permit small optical cavities to be employed. This has the added advantage that the size of the detection system as a whole can also be reduced.

In the illustrated embodiment, a prism is used as the reflective element 24. The prism 24 has a TIR face or surface 26 where sensing is performed, and its entrance and exit faces are preferably at Brewster's angle in order to minimize loss. As is discussed above, other members or elements may be used instead of a prism to provide the TIR surface. The two-way light path within the cavity is indicated by line 27, which shows two-way arrows. The analyte 30 is mounted in any conventional manner at the TIR surface 26 so that it is within the region of the evanescent field of the light reflected by the TIR surface 26. Suitable mounting methods include direct, renewable or non-renewable chemical attachment, and other renewable methods such as using magnetic particles that are held against the surface by a magnetic field.

In the embodiment shown in FIG. 3, the mirror 20 still forms an entrance mirror, since light from the source 25 passes through it into the resonant cavity, but light no longer is transmitted through the mirror 22. In other embodiments of the invention, which are described below, the light source 25 is included between the mirrors 20, 22, in the optical path. Depending on the embodiment, neither, one, or both of the mirrors 20, 22, will partially transmit, or will be partially or wholly reflective.

In this embodiment, it is assumed that the analyte either fluoresces naturally in the presence of electromagnetic excitation, or is provided with a fluorescing tag such as a fluorophore. As is mentioned above, the evanescent intensity $I_{circ}$ is many orders of magnitude larger than the incident intensity $I_{inc}$. Because of this, the degree of electromagnetic excitation within the evanescent field region at the TIR surface will also be many orders of magnitude greater than the degree of excitation that can be obtained from the incident light. The evanescent field will therefore either cause detectable fluorescence in much smaller amounts of analyte than are needed by conventional systems, or will be able to cause equivalent detectable fluorescence using much less source optical power.

Fluorescence from the analyte 30 is indicated in FIG. 3 by three outward-radiating arrows and is detected by a conventional fluorescence detector 34. The fluorescence detector 34 may be any known device that generates an electrical output signal that corresponds to the intensity of light from fluorescence that strikes its detection surface or element. The fluorescence detector 34 is preferably connected to a processor 36, which applies known methods to convert the signals from the detector 34 to a form suitable for transmission to another system and/or for display on a conventional display device 38.

Fluorescence is a non-coherent, linear frequency conversion of light. It can be shown that the intensity of fluorescence is directly proportional to the amount of sample present within approximately one optical wavelength of the TIR surface 26. Other types of light generation within the sample, such as non-linear and coherent light generation, may also be detected using the invention, in which case suitable conventional light detectors may still be used as the detector 34. The key advantage of the method according to the invention, regardless of the type of light that is generated within the sample, is its highly efficient use of available laser energy, which decreases the minimum detectable surface concentration by orders of magnitude.

According to the invention, the gain medium or source 25 (including other conventional optics), the resonator, and the fluorescence detector 34 may be manufactured into a single, compact monolithic device. Such a device would consume very little electrical power yet would still have a sensitivity that is the same or greater than existing devices. As in other embodiments of the invention, waveguides or fibers may be used as the reflective element 24 in place of the prism shown in FIG. 3.

Figure 4:
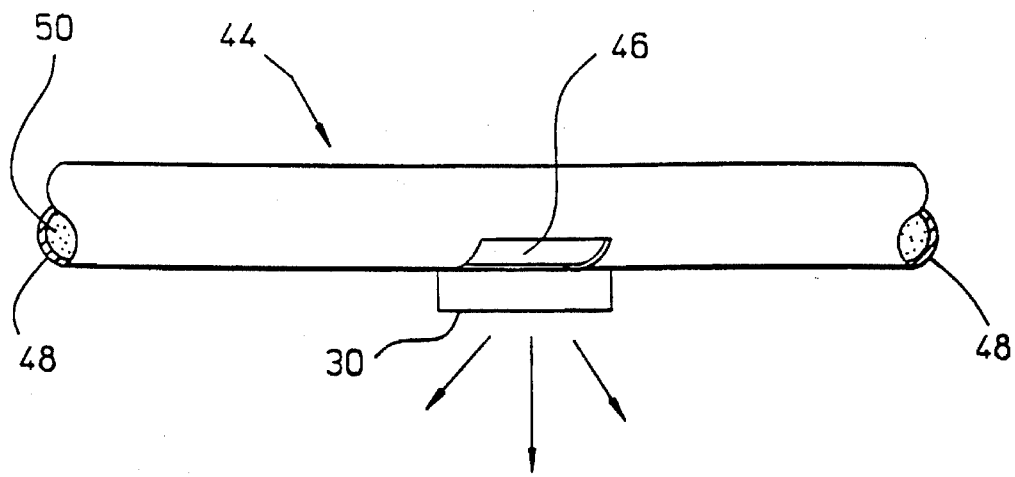
FIG. 4 illustrates a TIR surface created on a reflective element that has optical gain.

FIG. 4 illustrates an embodiment of the invention that increases the enhancement factor of the resonator by including a reflective element that also has optical gain ($\alpha<0$). In this embodiment, the resonator comprises a fiber laser 44 as a gain medium (for clarity, only a portion of the fiber of this otherwise known device is illustrated), in which a TIR surface 46 is created by removing a portion of cladding 48 that typically surrounds the actual optical fibers 50. The light source, mirrors, and detection and processing circuitry are not shown for the sake of simplicity only; these elements may be the same —physically and/or functionally—as those described above for the embodiment shown in FIG.

Since a fiber laser typically has optical gain, the evanescent field in the unclad region forming the TIR surface will be very large. Sensing of fluorescence (in applications using fluorescing analytes), is preferably carried out using detection and processing circuitry as shown and described for FIG. 3 with the analyte 30 mounted adjacent to the "window" in the cladding, that is, adjacent to the TIR surface 46.

Figure 5:
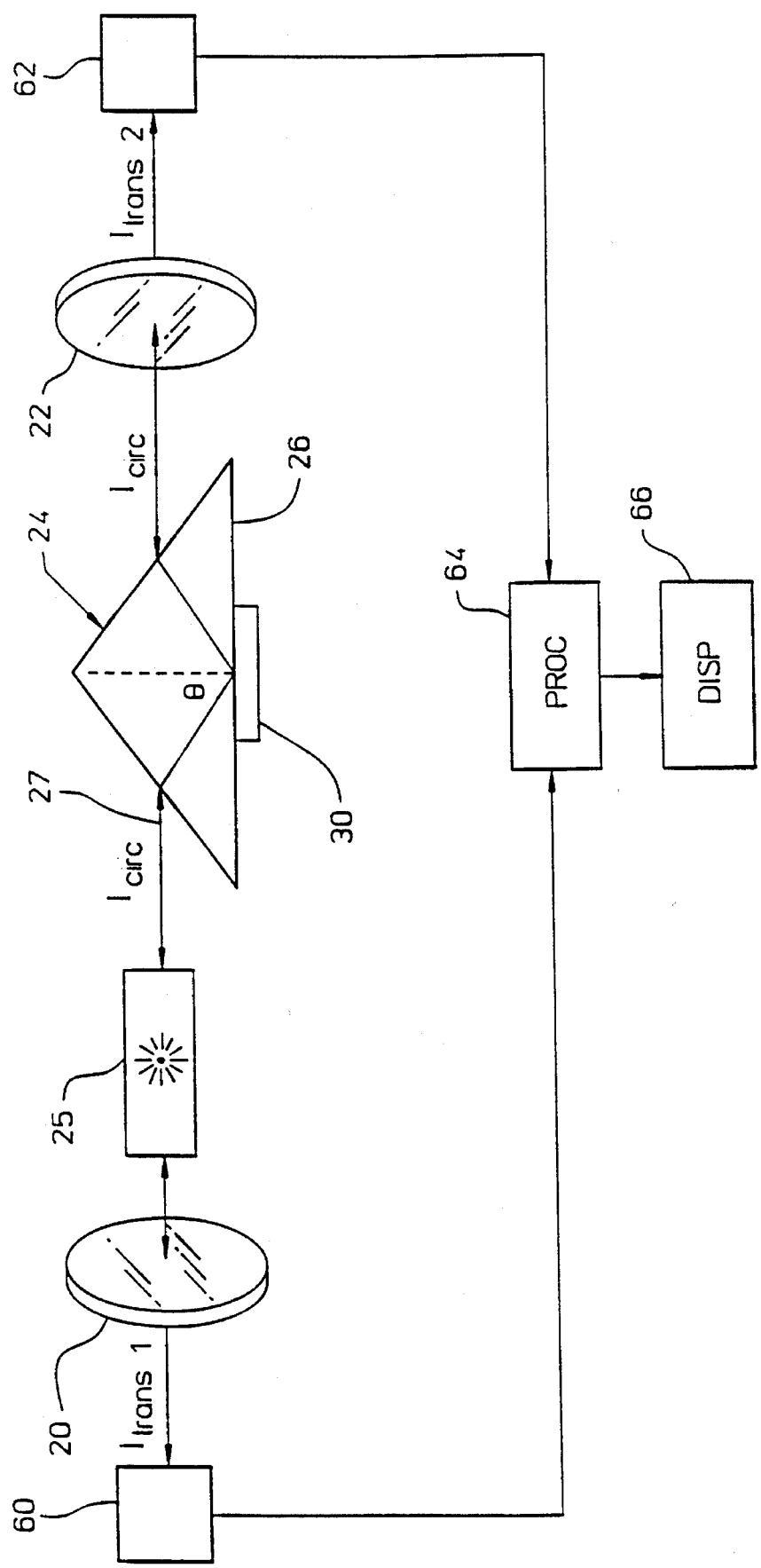
FIG. 5 shows schematically an embodiment of the invention similar to that shown in FIG. 3, but in which the light source is located within the resonator cavity.

It is also possible according to the invention to move the source 25 within the resonant cavity of FIG. 3. FIG. 5 illustrates an embodiment of the invention in which this has been done. In this embodiment, the light source may require different conventional optics, but needed changes will be known to those skilled in the art. A suitable light source for this embodiment would be a helium neon laser tube. Helium neon lasers are commercially available that have circulating powers greater than 100 W, but are still quite compact. A suitable laser tube is manufactured, for example, by Particle Measurement Systems of Boulder, Colo., USA. Other types of lasers may, however, of course be used. Sensing of fluorescence is performed as for the embodiment shown in FIG. 3.

In the embodiments shown in FIGS. 3–5, the great intensity of the intracavity evanescent field is used to excite fluorescence of molecules in the vicinity of the TIR surface. That the detector according to the invention is able to detect trace amounts of an analyte from a surface sample offers great advantages in its own right, and these advantages are discussed above. Still another advantage, however, is that since even trace amounts of the fluorescing analyte can be detected, the fluorescence does not act as a significant loss mechanism for the resonator, and in any event causes much less loss than the samples required in systems such as Godlevskii's.

As an example of the method according to the invention for detecting trace fluoroscopic analytes, consider a biochemical assay where a true-positive outcome results in the presence of a fluorophore in the evanescent field. If one uses a dye with a (large) molar absorption constant of 200,000 $M^{-1}cm^{-1}$ (such as CY5), then the surface concentration equivalent to a scatter loss of 300 ppm is about 0.5 pmole $cm^{-2}$ (corresponding to about $6\times10^9$ particles/$mm^2$). This scatter loss is enough to reduce the circulating intensity of a practical resonator by 50%. This dye concentration is close to the theoretical maximum one can covalently bind to a suitable surface. For example, unamplified DNA detection employs up to three orders of magnitude lower concentration. Note that as the absorption constant decreases the number density of particles necessary to perturb the intracavity field increases. This determines the limit of sensitivity of techniques such as Godlevskii's, which rely on absorption.

The Godlevskii/Kopytin device uses "frustrated" total internal reflection (FTIR), which means that it deliberately lets light out of the laser cavity. It needs to create a loss mechanism since its detection method is based on sensing loss. Because the Godlevskii device deliberately introduces loss, light must "bounce" as many times as possible against different points on the TIR surface; each bounce acts as a sensing point. This is necessary in order for as much light as possible to make it past the TIR boundary and be absorbed, and thereby to create a detectible loss. Multiple bounces are required for each analyte to be detected.

In devices such as Godlevskii's, reduction of the intensity due to absorption is therefore not only acceptable, it is also necessary in order for the system to operate properly. Since the Godlevskii device relies on sensing absorption losses, there must be enough of the material, such as the dye, to absorb enough energy to perturb the intracavity field. If one were to attempt to reduce the amount of dye to below the point at which the field is perturbed, then the absorption loss would be so small as to be undetectable by the Godlevskii system. Furthermore, the Godlevskii system is specifically designed for detection of gases or aerosol particles, and not for liquids or biological materials. For reasons of both structure and method, the Godlevskii system is therefore unsuitable for use in, for example, unamplified DNA detection.

In contrast, this invention detects concentrations well below (in most cases, orders of magnitude below) the point at which the field is perturbed, and makes unamplified DNA detection possible. Unlike systems such as Godlevskii/ Kopytin's, this invention does not frustrate the total internal reflection, since the invention does not rely on absorption loss for detecting fluorescence. Furthermore, since the invention actually minimizes loss, only one bounce on the TIR surface is needed for sensitive detection of fluorescence, or for the other optical characteristics, described below, that are detected and provide an indication of the presence and amount of the target substance contained within the sample at the TIR surface. In other words, light need only be reflected at the TIR surface at a single point (the small region corresponding in size to the cross-section of the light beam).

Fluorescence is only one of a class of optical probe techniques that rely on light intensity and changes or conversions in the light frequency, and that can use the invention. Other examples of linear phenomenon include Raman scattering or surface-enhanced Raman scattering, which are widely used surface sensing techniques. Other non-linear techniques in this class could also be used to advantage; these include second-harmonic generation and simulated Raman scattering. Nonlinear optical effects depend on the square or the cube of light intensity and would therefore benefit even more than fluorescence from the increase in intracavity intensity that the invention provides.

When using the invention as a fluorescence-based detector, one first pre-treats the TIR surface (outside the cavity) with chemicals or other substances that are known to bind the material one wishes to test for. Typical binding agents include nucleic acid, DNA, and proteins. A fluorescent tag is then applied to the substance(s) to be detected (which have a known chemical structure) in the test sample, assuming the substance does not fluoresce naturally. Pre-treatment in these forms creates a target complex, which includes the target substance to be detected, the fluorescent tag and possibly also binding agents. In cases in which pretreatment is not necessary, for example, where the target substance itself fluoresces, the target complex will consist of the target substance alone. Pretreatment of a surface and fluorescent tagging are well-known techniques in detection technology and any known methods may be used for these steps.

The sample is then introduced in any known manner to the pre-treated TIR surface. If none of the fluorescently tagged material to be detected is present in the sample, none will attach to the binding agent and there will be no fluorescence at the TIR surface. The more of the target substance is present, the more will bind to the binding agent and the greater the fluorescence will be. The fluorescence detector 34 senses the fluorescence and generates an output signal corresponding to the intensity of the detected fluorescence, which in turn corresponds to the amount of the target substance that is in the sample and bound at the TIR detection surface.

Note that the invention is able to excite and detect fluorescence generated very near the TIR surface, even within the thickness of one molecule of the binding agent and one molecule of the target substance. Of course, a thicker layer of the target substance will lead to even more fluorescence, but because the invention uses the greatly increased intensity in the evanescent field, much less of the target material can be detected than must be present for detection using loss-based systems such as Godlevskii/ Kopytin's.

As the discussion above brings out, an optical resonator as used in the invention offers an increase by several orders of magnitude in sensitivity for intensity-dependent sensing (such as fluorescence detection) as compared to known methods and devices. It is also more compact and uses orders of magnitude less electrical power.

Changing the angle of incidence of light at the TIR surface within the cavity changes the 1/e decay depth of the evanescent field. This in turn changes the depth above the TIR surface within which the sample is probed for the presence of the target substance. It is therefore advantageous to optimize the angle of incidence for any particular application of the invention. The choice of optimiztion method will depend on the intensity of available fluorescence compared with the intensity of the background light. One can measure the intensity during calibration either with the same detector 34 used for actual sensing or with a separate, conventional detector.

In the simplest case, the fluorescence is much larger than the background light. In this case, one sets the angle of incidence at any initial angle, and then changes the angle (for example, by rotating the prism) until a maximum intensity is sensed. The angle of incidence is then set at the angle for which the maximum intensity is achieved.

In the more common case, however, the intensity of fluorescence will be much less than the background intensity. In such case, one may use a conventional optical filter in front of the detector. The filter lets the fluorescence pass, but very heavily blocks the background light. The filtered background makes up part of the fluorescence signal, so in order to maximize the filtered fluorescence signal while minimizing the unfiltered fluorescence, one can choose an initial angle, measure the filtered and unfiltered intensity, then change the angle and repeat the measurements until an optimum angle is achieved. Experiments indicate that this method works well even when the background is one million or more times more intense than the fluorescence.

If the filtered background intensity is so great that it is still a very large component after filtering, one can use a control section (without a fluorophore) on the TIR surface. In this case, the filter is left in place during the measurement. Fluorescence from the control section and from a section with flourophore are measured as a function of the angle of incidence. The optimal angle is then chosen to be the angle where the difference in the signal between the control section and the fluorescence section is a maximum. This calibration method requires a TIR surface with two sections, but this will normally not be a significant disadvantage since the angle of incidence needs to be set only once for any given application.

Sensing of Macroscopic Sample Properties

The invention is also highly effective at sensing macroscopic properties of the sample, which are based on changes in the refractive index of the surface sample, or on changes in the resonance frequency of the optical resonator, rather than on the presence of a fluorescent material. Examples of such embodiments follow.

Refractive Index Sensing

When there is a chemical change at the TIR surface the refractive index $n_s$ of the sample also changes. An example of this phenomenon is an assay for antibodies: an antigen is bound to the TIR surface and one determines the antibody concentration by measuring the change, $\Delta n_s$, in $n_s$ when the antibody binds to the antigen. What follows are several embodiments for measuring such a change in $n_s$ using a resonator similar to those shown in FIGS. 1 and 3–5.

Eqn. 1 shows that $R_p=1$ for angles of incidence greater than the critical angle. (See also FIG. 2a.) For fixed angles of incidence close to the critical angle, as $n_s$ increases, the value of $R_p$ suddenly drops. In other words, if the angle of incidence is set near (but above) the critical angle, small changes in $n_s$ will result in large relative changes in $R_p$. Alternatively, according to the invention, the sudden drop in $R_p$ is used to establish a sensitivity threshold.

Figure 6:
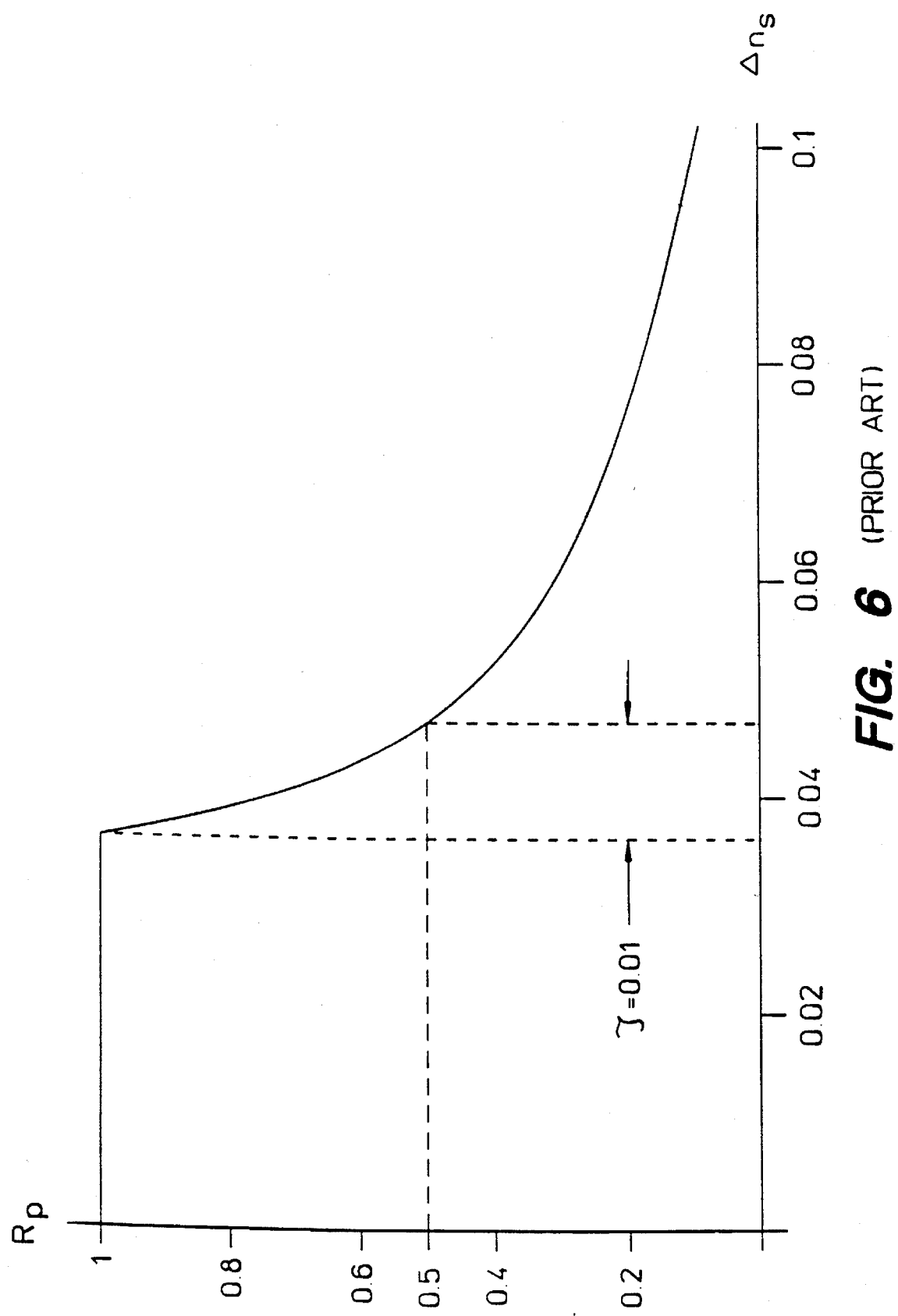
FIG. 6 illustrates the principle behind one method according to the invention for detecting an analyte; in particular.

FIG. 6 is a plot of the ratio $R_p$ of reflected intensity to incident intensity from a TIR surface between water and fused silica as a function of the increase $\Delta n_s$ in the refractive index of the water due to the presence of the analyte. In the hypothetical conventional system shown in FIG. 6, the TIR surface is not within a resonant cavity; hence, there are no mirrors. The angle of incidence is fixed at 70° and the sensitivity $\Im$ is defined as the increase in refractive index necessary to decrease the reflected signal by 50%. (Other threshold values may of course be used.) The point at which $R_p$ has dropped to 50% of its maximum value is also indicated.

As expected, below a certain value of $\Delta n_s$, there is total refection and $R_p=1$. As the amount of analyte increases, $\Delta n_s$ continues to increase, until at about $\Delta n_s, =0.037$, the reflected intensity (and thus $R_p$), begins to drop quickly. After a further change in $\Delta n_s$, of about 0.01, $R_p$ will have dropped by 50%. As FIG. 6 shows, once $\Delta n_s$ passes roughly 0.1, the $R_p$ curve flattens out and more of the analyte will not lead to a significant change in $R_p$. FIG. 6 thus shows that, when the TIR surface is not within a resonant cavity and a sensitivity threshold of 50% is used, the refractive index must change by roughly 0.01 before the system senses the presence of the analyte.

Figure 7:
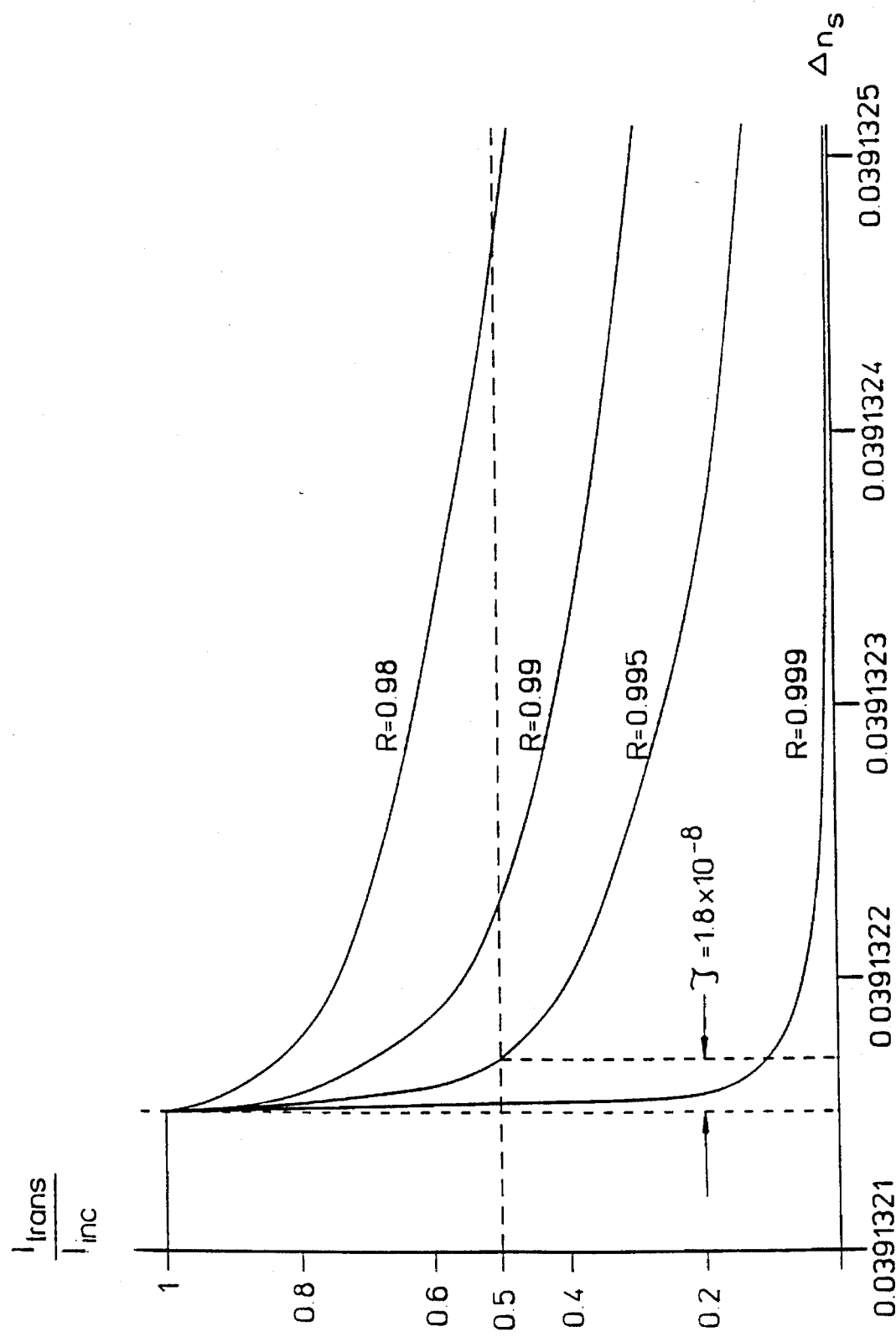
FIG. 7 illustrates graphically the effect on the sensitivity of the detector according to the invention of changes in mirror reflection; in particular, FIG. 7 plots the ratio of transmitted light intensity ($I_{trans}$) to incident light intensity ($I_{inc}$) for a TIR surface as a function of changes in the refractive index ($\Delta n_s$) for a family of different mirror reflection coefficients.

In contrast to the mirrorless, non-resonant system of FIG. 6, FIG. 7 shows a plot of the ratio of the intensity $I_{trans}$, transmitted through the resonator to the incident intensity $I_{inc}$ as a function of increase $\Delta n_s$ in refractive index of the water due to the presence of the analyte, also for a TIR surface between fused silica and water. In this case, however, the TIR surface is placed inside a resonator as according to the invention; this general configuration of the invention is depicted schematically in FIG. 1. The results of FIG. 7 can be compared with those illustrated in FIG. 6 to show the increase in sensitivity that the invention provides.

In FIG. 7, the ratio $I_{trans}/I_{inc}$ is evaluated for several mirror reflection coefficients, R, assuming that both mirrors are identical. (This assumption is not necessary to the invention; it is made solely for purposes of simplicity and clarity of explanation of the principle of the invention.) As before, the angle of incidence on the intracavity TIR surface is fixed at 70° (other angles may also be chosen). According to the invention, the intensity transmitted by the resonator is measured as a function of $\Delta n_s$ which can be calculated using Eqn. 5.

Note that for R=0.995, then $\Im=1.8\times10^{-8}$. In other words, even using only readily available, medium-reflectivity mirrors (R =0.995), the system according to the invention demonstrates a theoretical increase in sensitivity of more than five orders of magnitude $(0.01/1.8\times10^{-8} \approx 5.5\times10^5)$ as compared with the non-resonant system whose theoretical results are plotted in FIG. 6. Since mirrors with R=0.99998 are readily available on the commercial market, this increase in sensitivity can be made even greater, and is a significant improvement over the resolution of, for example, known waveguide interfero-meters, which is on the order of only $10^{-7}$.

As FIG. 7 shows, the higher the R value for the chosen mirrors is, the "steeper" is the drop-off of the $I_{trans}/I_{inc}$ curve, that is, the narrower is the $\Im$ band (once again, the amount $n_s$ must change enough to cause a decrease in $R_p$ of 50%). Depending on the application, however, it is not always true that higher R is "better." For example, assume that experience shows that the presence of a particular analyte usually causes a change in $n_s$ of about $3.0\times10^{-7}$ (corresponding to a change of three whole indicated units on the $\Delta n_s$ axis in FIG. 7). Assume further that an "all-or-nothing" indication of the presence of the analyte is undesirable for the particular application.

Mirrors with a reflectivity R=0.999 would then be a poor choice, since $I_{trans}/I_{inc}$ would drop from 1.0 to almost 0.0 as soon as any of the analyte were present. Instead, mirrors with R=0.990 or even 0.980 or something in between might be a better choice by providing good sensitivity to the presence of the analyte without being too sensitive to noise. For any given application of the invention, the proper mirror reflectivities can be chosen by standard experimentation methods.

In FIG. 7, the frequency of the input light is tuned to the resonant frequency of the resonator in order to satisfy Eqn. 6. This can be easily accomplished in practice by frequency locking the light source to the resonator, as is well known to those skilled in the art.

The dramatic increase in sensitivity over extracavity TIR is evident from a comparison of FIG. 6 and FIG. 7, and is due to the trapped light in the resonator "sampling" the same spot many times. The higher the mirror reflectivities are, the more the light is trapped and hence the greater is the sensitivity of the detector. For equal mirror reflection coefficients $R=R_1=R_2 =0.995$ (which represents easily obtainable and fairly inexpensive mirrors), the transmitted intensity is sensitive to a change in refractive index of about $2\times10^{-8}$.

Figure 8:
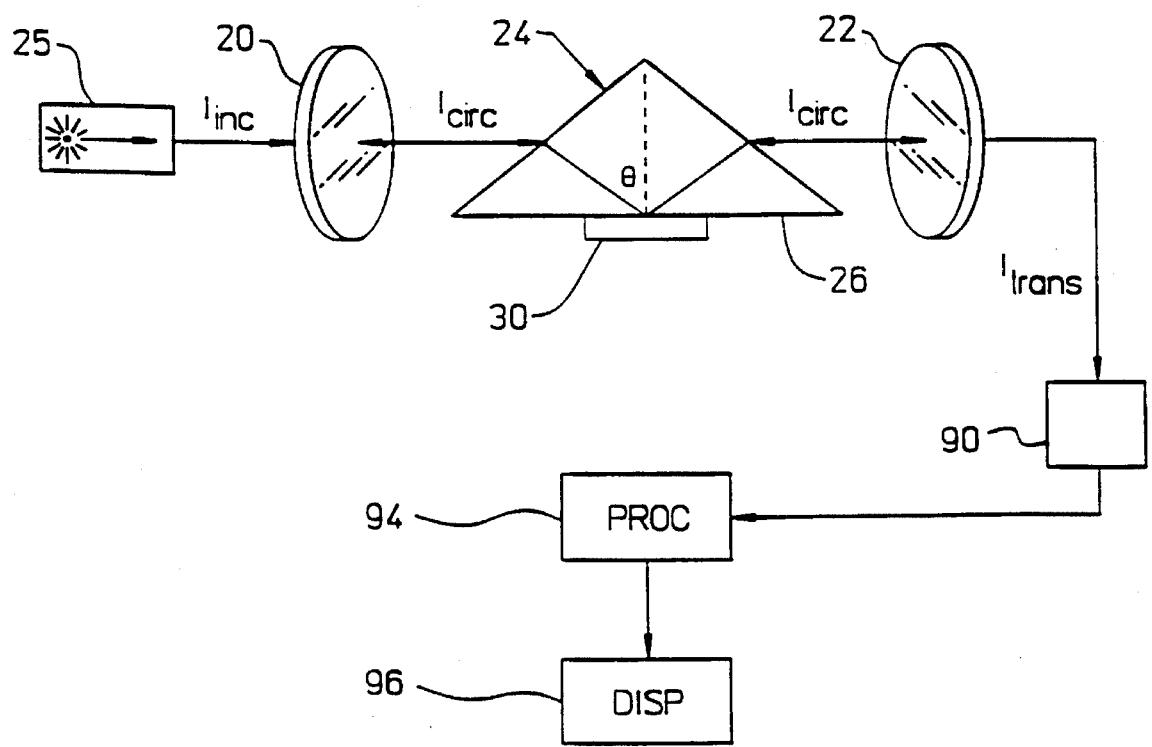
FIG. 8 is a block diagram of a system according to the invention for determining changes in transmitted light intensity in order to detect the presence of an analyte, for example, using the effect illustrated in FIG. 7.

FIG. 8 is a block diagram of a system according to the invention for determining changes in transmitted light intensity in order to detect the presence of an analyte, for example, using the effect illustrated in FIG. 7. Elements similar to those shown in other figures have the same reference numbers. In the system shown in FIG. 8, a conventional sensor 90 is provided in order to measure the light intensity $I_{trans}$, transmitted through the mirror 22. As before, conversion of the signal from the sensor 90 into a form, suitable for determining $I_{trans}/I_{inc}$ is carried out using conventional conversion and processing circuitry 94, with results displayed in any convenient format on a display 96.

If $I_{inc}$ is not known from the properties of the chosen light source 25, an additional conventional sensor (not shown) for measuring $I_{inc}$ may be connected to the processing circuitry 94 and added to the system shown in FIG. 8 either in the source 25 or between the source 25 and the entrance mirror 20. If needed, for example, if the system is to use different mirrors for different applications, the reflectivity coefficient(s) for the mirrors 20, 22, may be entered into the processing circuitry 94 in any conventional manner.

Figure 9:
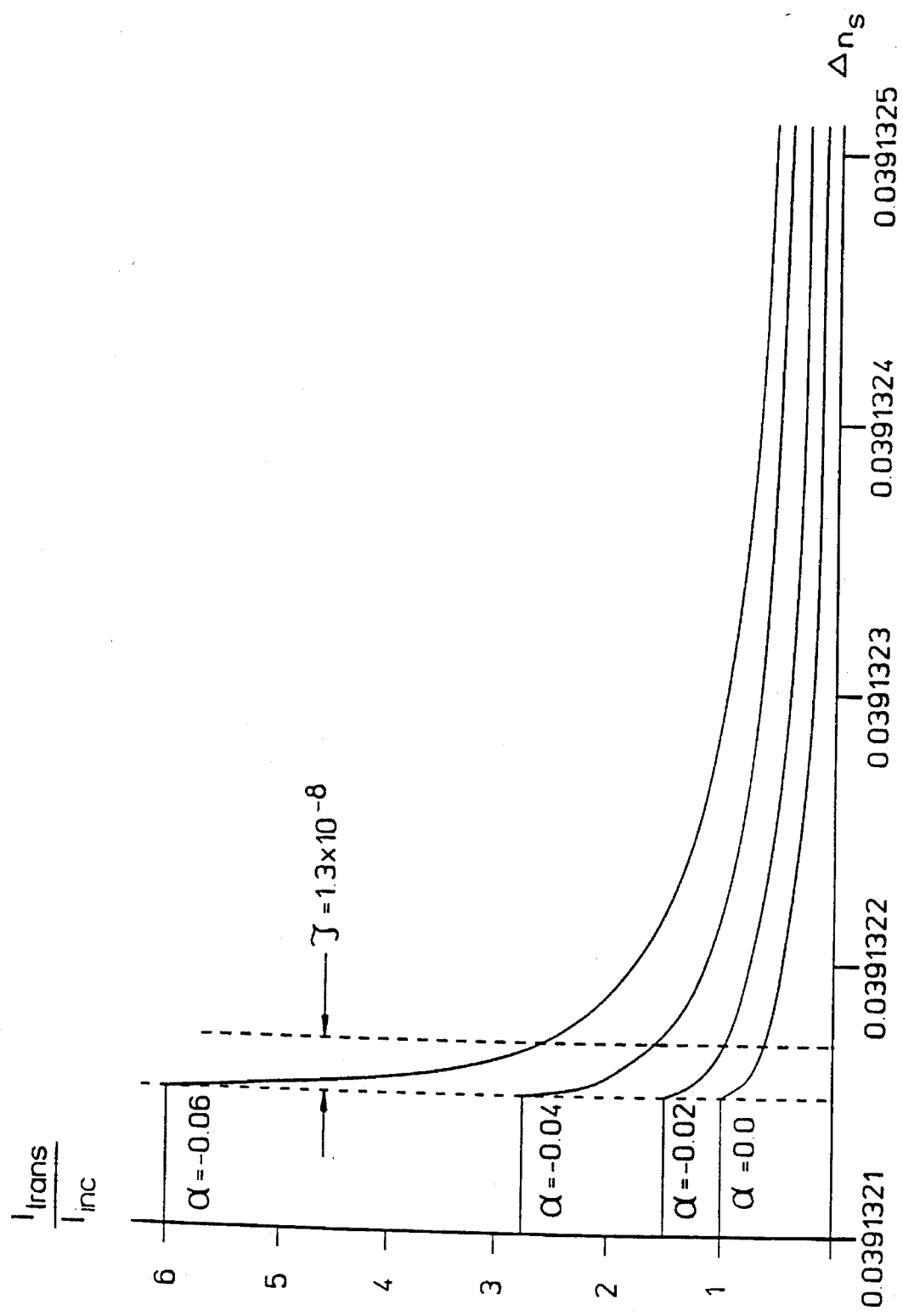
FIG. 9 is an example of a plot of $I_{trans}$, $I_{inc}$ as a function of $\Delta n_s$ for different intracavity gain factors in a detector according to the invention.

The invention also increases the sensitivity of a resonator with fixed mirror reflection coefficients, as can be seen by examining its sensitivity as a function of intracavity optical gain, $\alpha$. FIG. 9 is a plot of the ratio of the intensity $I_{trans}$, transmitted through the resonator, to the incident intensity $I_{inc}$ as a function of increase $\Delta n_s$ in the refractive index of the water due to the presence of the analyte, once again for a TIR surface between fused silica and water placed inside a resonator with a gain element as depicted in FIG. 5. The ratio is evaluated for several intracavity gains, α, assuming both mirrors are identical and have R=0.99. The angle of incidence on the intracavity TIR surface is once again fixed at 70°. Note that for α=−0.06, then $\mathfrak{I}=1.3\times10^{-8}$.

In FIG. 9, note that $I_{trans}$ is now larger than $I_{inc}$ due to amplification (α<0) within the resonator. As before, the frequency of the incident light is assumed to satisfy Eqn. 6. As FIG. 9 shows, as the gain increases, the sensitivity of the resonator also increases.

In the embodiment of the invention illustrated in FIG. 5, the invention applies the principle illustrated in FIG. 9 by providing a conventional sensor 60, 62 preferably for each mirror 20, 22 in order to measure the light intensity $I_{trans1}$, $I_{trans2}$ that leaks out of the respective mirrors, rather than the fluorescence of the analyte. Current values of the optical gain α, the detection threshold (for example, 50% decrease in intensity), and the reflectivity of the mirror(s) (as well as of $I_{inc}$ if known beforehand), are input to the processing circuitry 64 in any conventional and convenient manner.

The resonator could work in either stand-alone mode (as shown in FIG. 3) or as a regenerative amplifier (that is, with a gain medium added, so that α<0). Furthermore, by combining the embodiment illustrated in FIG. 5 with the fluorescence-detecting embodiment of FIG. 3 (by simply including the fluorescence detector 34 and accompanying processing circuitry as shown in FIG. 3), a single combined embodiment could measure the transmitted intensity when low sensitivity is required and measure fluorescence when high sensitivity is required.

As before, conversion of the signals from the sensors 60, 62, into a form suitable for determining $I_{trans}/I_{inc}$ is carried out using conventional conversion and processing circuitry 64, with results displayed in any convenient format on a display 66. It is also possible to not measure light transmission from both ends of the system, but rather only through one mirror (for example, $I_{trans1}$ through mirror 20); however, in general such a configuration will not be as accurate for intracavity light sources 25 as the "double-ended" sensor arrangement shown in FIG. 5.

FIG. 5 shows a system in which there are two mirrors and two sensors and the light source 25 is located within the resonance cavity. The system may, however, also be configured with the light source outside of the resonance path (see, for example, FIG. 8 below), with a single sensor for sensing the light that is transmitted through the mirror on the other side of the reflective element from the light source.

Consider now once again FIGS. 5, 7 and 8. The method by which one calibrates and the embodiment of the invention shown in FIG. 7 is as follows. One first determines what sensitivity $\mathfrak{I}$ one desires for the particular application and chooses mirrors with suitable reflectivities (for example, based on theoretical or experimental data such as that shown in FIG. 7).

Using a neutral sample at the TIR surface (that is, a sample that does not contain the molecules to be detected and thus has a refractivity index $n_s$ less than that which it has when it contains these molecules), one adjusts any or all of the reflective elements 24, the mirror(s), the light source, and any intermediate reflective or refractive elements (if included in a given application), so that the angle of incidence at the TIR surface 26 is at or just greater than the critical angle.

Refer now once again to FIG. 7. A preferred way of calibrating the detector is to adjust the angle of incidence so that the system is on the TIR "plateau" (where $I_{trans}/I_{inc}=1$).

One then decreases the angle of incidence (approaching the critical angle) until one notices (either by visual inspection of an output display or by automatic means such as the processing circuitry 64, 94) that $I_{trans}/I_{inc}$ just begins to drop. The angle is then increased until $I_{trans}/I_{inc}$ once again is at a predetermined initial setting, which is preferably at or just below 1.0, for example, ≧0.95, ≧0.99, or some other chosen initial value. At this point, the system is calibrated so that the angle of incidence and the refractive properties of the sample attached adjacent the TIR surface are such that the system is at or near (for example, within a range of 0.1% to 1.0%), the chosen approximate value of $\mathfrak{I}$.

The actual test sample is then introduced adjacent to the TIR surface 26, within the evanescent field of the light. If the test sample contains enough of the analyte, the value of $I_{trans}/I_{inc}$ sensed by the system will drop below the chosen threshold (for example, 0.5) and the system, via the processor 64, 94 and the display 66, 96 (if included) will indicate that the analyte is present in the test sample.

It is not necessary fix a threshold and for the system to output a "yes/no" type result; rather, the actual measured value of $I_{trans}/I_{inc}$, or some approximation of this value, may be displayed to the user. In such a "continuous" or "non-automatic" case, the user may then decide for herself whether there is sufficient indication that the analyte is present.

The sensitivity of the embodiments proposed above can be compared to theoretical limits of other techniques based on refractive index change. For example, Lukosz, W. in "Principles and sensitivities of integrated optical and surface plasmon sensors for direct affinity sensing and immunosensing," Biosensors and Bioelectronics, 6, 215 (1991), has shown that interferometric waveguides are sensitive to changes in $n_s$ of $1\times10^{-6}$ and Liu, Y., Hering, P., and Scully, M. O., in "An integrated optical sensor for measuring glucose concentration," Appl. Phys, B54, 18 (1992), have similarly reported a sensitivity to changes in $n_s$ of $6\times10^{-6}$. As FIG. 7 indicates, the achievable sensitivity of the invention is more than an order of magnitude greater than even the theoretical limits of such known devices.

Resonant Frequency Sensing

The variable affected by the above approach is the reflectivity of the prism, $R_p$. Adding analyte to the TIR surface will, however, also change the resonant frequency, $\omega_m$, of the optical resonator (see Eqn. 6). According to another embodiment of the invention, this change is determined and is also used a measure of the amount of analyte present: the larger the change in $\omega_m$, the more analyte is presumed to be present.

Figure 10:
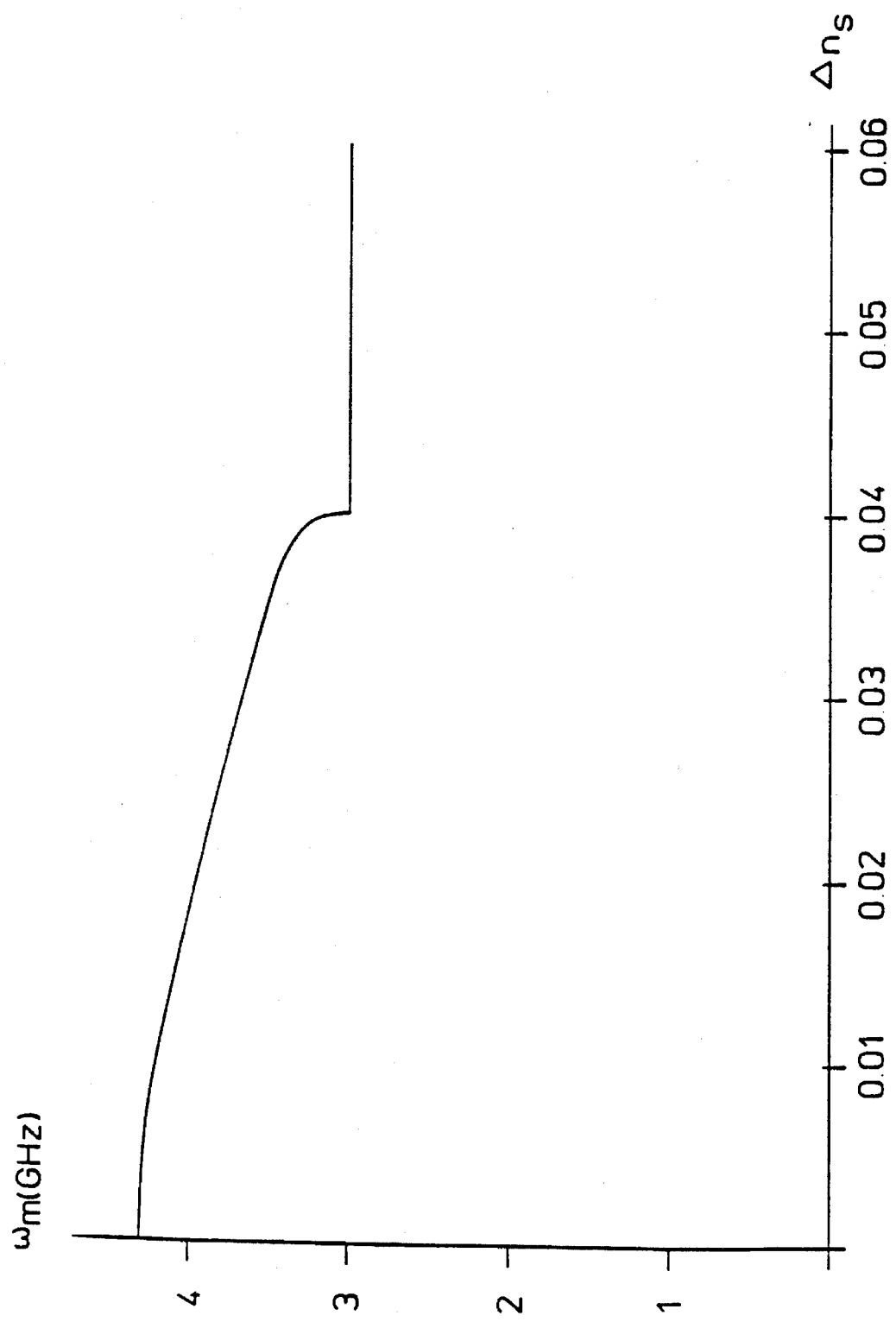
FIG. 10 is an example of a plot of a resonant frequency ($\omega_m$) as a function of $\Delta n_s$ for an optical resonator incorporating a TIR surface according the invention.

FIG. 10 illustrates the relationship between $\omega_m$ and $\Delta n_s$, for a TIR surface between water and fused silica where the angle of incidence θ of the intracavity beam on the TIR interface is 70°. As $\Delta n_s$ increases, $\omega_m$ decreases or remains constant, but the critical angle for TIR increases until at $\Delta n_s \approx 0.04$ the critical angle equals the angle of incidence, that is, 70°. Beyond this point there is no TIR and hence no change in $\omega_m$. Note that the slope of the curve is greatest near $\Delta n_s \approx 0.04$.

FIG. 8 also illustrates an embodiment of the invention that directly measures changes in $\omega_m$, using a conventional scanning Fabry-Perot interferometer (FPI) as the sensor 90. The sensitivity of this embodiment depends on the resolution or finesse, f, of the FPI 90, which is a well-known property given by f≈π/T, where T is the power transmission of the FPI mirrors. One can fairly readily purchase mirrors that have T as low as 20 ppm; this yields f≈1.5×10⁵. For a 3 GHz free spectral range, the FPI has a resolution of 20 kHz. The sensitivity of this technique also depends on (the "slope" of the curve in FIG. 10), which is a function of the angle of incidence, θ, on the TIR surface.

Numerical calculations have shown that, using this embodiment of the invention, a sensitivity of $\Im=5\times10^{-6}$ can be achieved for θ=80°, and that $\Im=7\times10^{-7}$ may be resolved if one operates closer to the initial critical angle of θ=67°.

The use of a scanning FPI as the sensor 90 does not exclude construction of the invention as a miniature monolithic device. Jerman et al., for example, have used micromachining techniques to build a scanning FPI that is only 5 mm square and other design improvements in FPI technology are expected to provide FPI devices suitable for use in the invention when implemented as a monolithic device.

We claim:

1. A method for detecting a target substance in a sample comprising the following steps:

A. mounting a totally internally reflecting (TIR) member within a resonance cavity of an optical resonator;

B. creating an evanescent field region at a TIR surface of the TIR member by directing light from a light source onto the TIR surface at an angle greater than a critical angle so that the light is reflected substantially without loss by the TIR surface;

C. positioning the sample to extend within the evanescent field region; and

D. substantially non-absorptively detecting a predetermined macroscopic optical characteristic of the sample corresponding to the amount of the target substance that is in the sample in the evanescent field region.

2. A method as in claim 1, including the step of focussing the light from the light source onto a single point of reflection on the TIR surface.

3. A method as defined in claim 1, further including the step of optically frequency-locking the semi-conductor light source to the cavity.

4. A method as in claim 1, including the further steps of generating the light using a gain medium and positioning the gain medium outside of the resonance cavity.

5. A method as in claim 4, in which the light source is a semi-conductor.

* * * * *